(12) United States Patent
Gupta et al.

(10) Patent No.: US 9,925,343 B2
(45) Date of Patent: Mar. 27, 2018

(54) LUER CONNECTION ADAPTERS FOR SYRINGES

(71) Applicant: Unitract Syringe Pty Ltd, Sydney (AU)

(72) Inventors: Jyoti Gupta, Atlanta, GA (US); Brandon J. McKee, Nesquehoning, PA (US)

( * ) Notice: Subject to any disclaimer, the term of this patent is extended or adjusted under 35 U.S.C. 154(b) by 0 days.

(21) Appl. No.: 14/453,354

(22) Filed: Aug. 6, 2014

(65) Prior Publication Data
US 2015/0045744 A1    Feb. 12, 2015

Related U.S. Application Data

(60) Provisional application No. 61/863,098, filed on Aug. 7, 2013.

(51) Int. Cl.
| | |
|---|---|
| *A61M 5/00* | (2006.01) |
| *A61M 5/32* | (2006.01) |
| *A61M 5/31* | (2006.01) |
| *A61M 5/34* | (2006.01) |
| *A61M 5/50* | (2006.01) |

(52) U.S. Cl.
CPC .......... *A61M 5/347* (2013.01); *A61M 5/3134* (2013.01); *A61M 5/322* (2013.01); *A61M 5/345* (2013.01); *A61M 5/5086* (2013.01); *A61M 2005/3104* (2013.01);
(Continued)

(58) Field of Classification Search
CPC .......... A61M 2005/323; A61M 5/3221; A61M 5/345; A61M 5/347; A61M 5/5086; A61M 2205/0216
See application file for complete search history.

(56) References Cited

U.S. PATENT DOCUMENTS

| | | |
|---|---|---|
| 2,656,836 A | 10/1953 | Hickey et al. |
| 4,220,151 A | 9/1980 | Whitney |

(Continued)

FOREIGN PATENT DOCUMENTS

| | | |
|---|---|---|
| EP | 1923086 A1 | 5/2008 |
| EP | 2015802 A2 | 1/2009 |

(Continued)

OTHER PUBLICATIONS

International Search Report and Written Opinion, mailed Dec. 11, 2014, in International Application No. PCT/US2014/049962, filed Aug. 6, 2014.

(Continued)

*Primary Examiner* — Rebecca E Eisenberg
(74) *Attorney, Agent, or Firm* — Wiley Rein, LLP

(57) ABSTRACT

A connector mountable to a syringe barrel has a proximal barrel-engaging portion, a distal luer fitment portion, and a fluid aperture therethrough. The barrel-engaging portion of the connector includes an axial ledge configured to abut the axial distal edge of a glass syringe barrel. The connector facilitates mounting a luer assembly to the barrel. The luer assembly may be a tip cap, a luer needle assembly, or a luer needle-less assembly, having a complementary luer fitment for connection to the luer fitment portion of the connector. The connector and syringe may further include an immobile, compressible needle seal. The needle seal is adjacent to or engageable with the barrel-engaging portion of the connector.

13 Claims, 5 Drawing Sheets

(52) U.S. Cl.
CPC .............. *A61M 2005/3106* (2013.01); *A61M 2005/3231* (2013.01); *A61M 2205/0216* (2013.01)

(56) References Cited

U.S. PATENT DOCUMENTS

| | | |
|---|---|---|
| 4,294,250 A | 10/1981 | Dennehey |
| 4,607,868 A | 8/1986 | Harvey et al. |
| 5,122,117 A | 6/1992 | Haber et al. |
| 5,322,515 A | 6/1994 | Karas et al. |
| 5,533,708 A | 7/1996 | Atkinson et al. |
| 5,555,908 A | 9/1996 | Edwards et al. |
| 5,620,427 A | 4/1997 | Werschmidt et al. |
| 5,624,402 A | 4/1997 | Imbert |
| 5,651,776 A | 7/1997 | Appling et al. |
| 5,807,345 A | 9/1998 | Grabenkort |
| 6,004,299 A | 12/1999 | Arai et al. |
| 6,027,482 A | 2/2000 | Imbert |
| 6,190,364 B1 | 2/2001 | Imbert |
| 6,280,418 B1 | 8/2001 | Reinhard et al. |
| 6,569,118 B2 | 5/2003 | Johnson et al. |
| 7,090,657 B2 | 8/2006 | Tang |
| 7,695,458 B2 | 4/2010 | Belley et al. |
| RE43,597 E | 8/2012 | Johnson et al. |
| 9,302,056 B2 | 4/2016 | Thorley et al. |
| 2011/0015578 A1* | 1/2011 | Lowke .................. 604/192 |
| 2013/0338575 A1* | 12/2013 | Glocker et al. ........... 604/57 |

FOREIGN PATENT DOCUMENTS

| | | | |
|---|---|---|---|
| WO | WO0174424 | 10/2001 | |
| WO | 2012116792 | * 9/2012 | ............ 604/57 |

OTHER PUBLICATIONS

International Preliminary Report on Patentability, mailed Jul. 30, 2015, in related International Application No. PCT/US14/50116, filed Aug. 7, 2014.

European search report dated Feb. 14, 2017, by EPO in related European patent application No. 14835403.8.

* cited by examiner

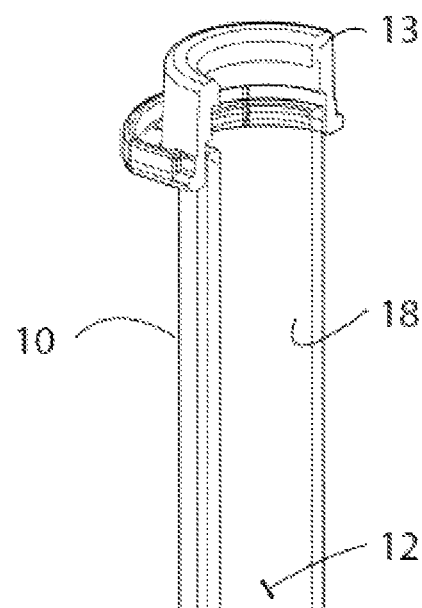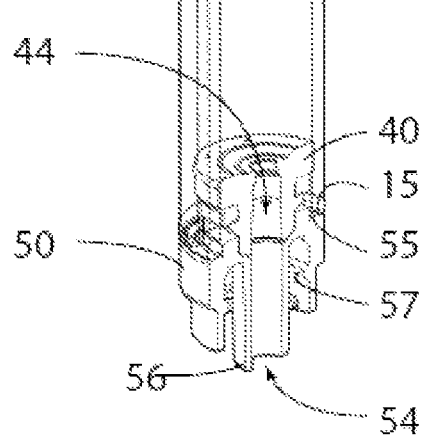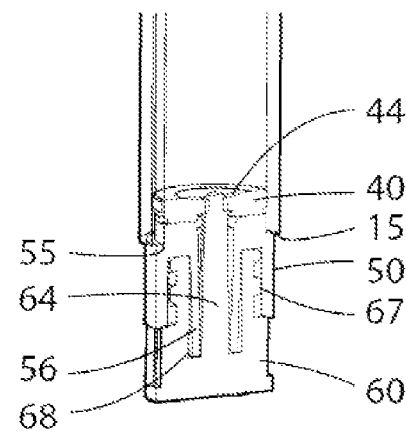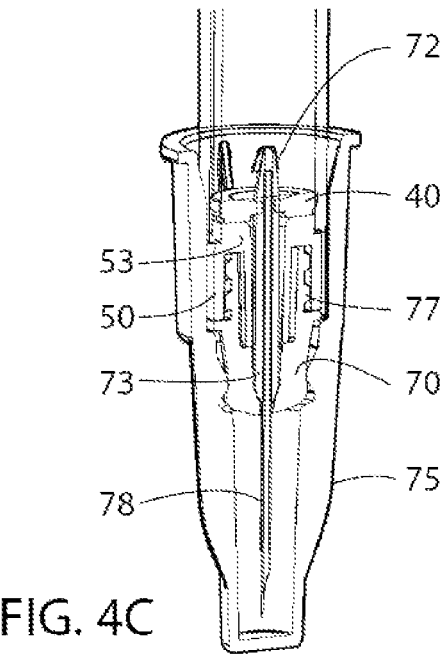
FIG. 4A  FIG. 4B  FIG. 4C

LUER CONNECTION ADAPTERS FOR SYRINGES

RELATED APPLICATIONS

This application claims priority benefit of U.S. Application No. 61/863,098, filed 7 Aug. 2013, which is incorporated fully herein for all purposes.

FIELD

The embodiments described herein relate to syringes. More particularly, the embodiments provide for luer connections configured to connect to syringe barrels and provide a luer fitment capable of connecting to fluid lines, selectable needle attachments, and the like, for delivery of fluids.

BACKGROUND

Today's healthcare practitioners are usually provided with medical devices that are ready to use, because the devices are sterilized during manufacture. This is particularly true of syringes that are used to administer parenteral drugs and other medical solutions. A syringe typically includes a plastic barrel having a substantially closed end and an opposite open end. The open end is sealed by a slidable piston plunger. The closed end of the syringe has a dispensing port communicating with a male luer fitment, for dispensing the contents of the syringe. The syringe, as manufactured, may be prefilled with a liquid, part-filled with a lyophilized powder, or empty, for example. A removable end cover, such as a luer cap is placed over the luer fitment during manufacture so as to seal the contents within the barrel. Prefilled syringes are advantageous in avoiding confusion whether a vial is multidose or single dose, or confusion regarding which diluent should be used with a given lyophilized or powder medicament, and may provide a suitable housing for storage and shipping of sensitive pharmaceuticals such as biologics. Furthermore, use of prefilled syringes, particularly those with safety mechanisms, limits health professionals exposure to used syringes, inadvertent needlestick injuries, and possible exposure to infective pathogens or other contaminants.

Because of the increasing demand for prefilled syringes, there is a proportional increasing need syringes that are made or materials resilient to degradation or interaction with the pharmaceutical or other agent held within the syringe. Additionally, there are filled-on-demand substances that are not compatible with existing plastic syringes. In an attempt to overcome these issues, many syringe manufacturers have returned to the manufacture of glass syringes or syringes in which at least the barrel is glass. Current commercial versions of glass syringes have glass tips that are housed within plastic adapter structures for connection to syringes or other delivery means. These glass syringes have several disadvantages: the tips are fragile and may break during preparation or use, leading to potentially dangerous sharps; the syringes leak around imperfect seals between the glass and the adapter; plastic adapter structures may spontaneously disconnect from the glass tip; or the tips may clog due to the narrow nature of the configured glass tips.

Further, in developing syringes with luer connections, relatively complicated luer assemblies have been devised that are often adapted for a particular syringe barrel shape or configuration and cannot be readily mounted to a syringe barrel having a different shape or configuration. This is particularly a problem with glass syringe barrels which are generally in short supply, and typically lack the desired shape or configuration for mounting a luer assembly. Alternatively, the syringes may be manufactured with a pre-formed luer assembly, which adds substantial complexity and cost to the process for manufacture of such syringes. Therefore, there is increasing demand for resilient syringes with adequate connectors for needle and needle-less devices.

SUMMARY

The embodiments of the present invention provide for connectors that facilitate mounting of a luer assembly to a pre-formed resilient syringe barrel, such as, for example, a straight, glass barrel. The embodiments herein provide for a connector that is easily adaptable to a variety of syringe barrels and obviates the need to have a particular barrel shape or configuration for mounting a luer assembly thereto. Aspects of these embodiments provide for a relatively simplified luer assembly that comprises fewer or simpler components, thereby providing a user-friendly and safe syringe while keeping manufacturing costs to a minimum, or facilitating mass distribution of syringes. For example, the present embodiments permit the use of straight glass barrels, rather than glass barrels with formed distal tips which are significantly more costly to manufacture. Other aspects provide for efficient delivery of fluid contents, thereby minimizing waste of fluid contents.

In a one aspect, the embodiments provide a connector configured to couple with, mount to, or engage with, a syringe barrel, the connector comprising a body that includes a barrel-engaging portion, distal portion configured to engage a luer fitment, and an aperture disposed centrally and axially through the connector. As used in reference to the present embodiments, "adapter," "luer connection adapter," "lure connection" may be used interchangeably with "connector." The connector may also be configured to couple or mount to, or engage with, a needle assembly or a needle-less assembly. The connector may serve as a needle aperture. In at least one embodiment, the connector (e.g., a luer connection adapter) also includes a needle seal, which may be mounted within the barrel, for example, adjacent and proximal to the barrel-engaging portion of the connector, and further comprising an aperture positioned to communicate with the connector. In use, the needle seal may be compressible but substantially immobile. In a particular embodiment, the needle seal is engaged with a portion of the connector. Suitably, when the connector is coupled with a needle assembly, a cannula of the needle assembly is received or accommodated by, or extends through, the needle aperture of the connector.

Another embodiment provides for a syringe barrel comprising the connector and, optionally, the needle seal. Another embodiment provides for a syringe comprising the connector situated in a syringe barrel, optionally with the needle seal, and, optionally, a plunger.

An aspect of the embodiments provides a method of assembling all or part of a syringe comprising the novel connector. A further aspect provides a method of use of the syringe, including the step of delivering fluid contents of the syringe to a subject, such as a human. The syringe of the aforementioned aspects may be a syringe for connection, via luer lock connection, to an intravenous fluid line. A luer lock connection can be a conical or tapered connection having a screw-threaded mating configuration. The syringe can be a pre-filled syringe, a mixing syringe, a sequential delivery syringe, or the like.

BRIEF DESCRIPTION OF THE DRAWINGS

Non-limiting embodiments of the invention are described herein with reference to the following drawings wherein:

FIG. 4A to FIG. 4C are isometric sectional views of an embodiment showing a connector housed in a syringe barrel comprising a collar (FIG. 4A), a tip cap (FIG. 4B), and a needle assembly (FIG. 4C).

DETAILED DESCRIPTION

Figure 1A:
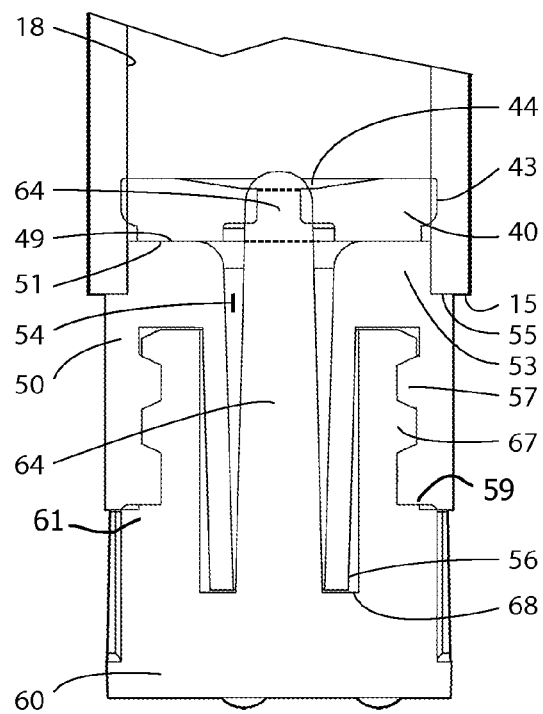
FIG. 1A is a sectional view of an embodiment of a connector assembly and a removable tip cap.

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and does not constitute any admission as to the correctness of the dates or contents of these documents.

As used herein and in the claims, the singular forms include the plural reference and vice versa unless clearly indicated otherwise by context. Throughout this specification, unless otherwise indicated, "comprise," "comprises" and "comprising" are used inclusively rather than exclusively, so that a stated integer or group of integers may include one or more other non-stated integers or groups of integers. The term "or" is inclusive unless modified, for example, by "either." Other than in the operating examples, or where otherwise indicated, all numbers expressing quantities of ingredients or reaction conditions used herein should be understood as modified in all instances by the term "about."

Unless otherwise defined, scientific and technical terms used in connection with the formulations described herein shall have the meanings that are commonly understood by those of ordinary skill in the art. The terminology used herein is for the purpose of describing particular embodiments only, and is not intended to limit the scope of the present invention, which is defined solely by the claims. The terms male and female may be used interchangeably to describe corresponding components or complementary aspects thereof and are not a limitation to either particular structure unless context clearly indicates otherwise.

As used herein to describe the relative positions of the components of the present embodiments, the terms "axial" or "axially" refer generally to a longitudinal axis "A" of the barrel of a syringe and plunger in which or around components are positioned, although not necessarily symmetrically there-around. The term "radial" refers generally to a direction perpendicular to axis A. The terms "proximal," "rear," "rearward," "back," or "backward" refer generally to an axial direction in the direction "P." The terms "distal," "front," "frontward," "depressed," or "forward" refer generally to an axial direction in the direction "D," toward the dispensing end of the syringe.

"Fluid" refers primarily to liquids, but can also include suspensions of solids dispersed in liquids (dispersions, suspensions, colloidal mixtures), emulsions, liposomal compositions, and gasses dissolved in or otherwise present together within liquids inside the fluid-containing portions of syringes.

As used herein, the term "glass" should be understood to include other similarly non-reactive materials suitable for use in a pharmaceutical grade application that would normally require glass (e.g., Type I borosilicate glass), including but not limited to certain non-reactive polymers such as cyclic olefin copolymers (COC) and cyclic olefin polymers (COP).

The term "plastic" may include both thermoplastic and thermosetting polymers. Thermoplastic polymers can be re-softened to their original condition by heat; thermosetting polymers cannot. As used herein, the term "plastic" refers primarily to moldable thermoplastic polymers such as, for example, polyethylene and polypropylene, or an acrylic resin, that also typically contain other ingredients such as curatives, fillers, reinforcing agents, colorants, or plasticizers, etc., and that can be formed or molded under heat and pressure. As used herein, the term "plastic" can include pharmaceutical grade non-reactive polymers or elastomers that are approved for use in applications where they are in direct contact with therapeutic substances, such that the plastics do not interact with the substances contacting the plastic and are not readily susceptible to leaching or gas migration under ambient temperature and pressure.

The term "elastomer," "elastomeric" or "elastomeric material" refers primarily to cross-linked thermosetting rubbery polymers that are more easily deformable than resilient plastics, are approved for use with pharmaceutical grade substances, and are not readily susceptible to leaching or gas migration under ambient temperature and pressure. It is appreciated in the art that particular elastomeric polymers are better suited for contact with pharmaceuticals than are some particular plastics, hence the elastomeric material can be a biocompatible material. As used herein, the term "elastomer," "elastomeric" or "elastomeric material" may also include other biocompatible materials, such as styrenic block copolymers (TPE-s), polyolefin blends (TPE-o), elastomeric alloys (TPE-v or TPV), thermoplastic polyurethanes (TPU), thermoplastic copolyesters, or thermoplastic polyamides, among other biocompatible materials which are approved for use with pharmaceutical grade substances, and are not readily susceptible to leaching or gas migration under ambient temperature and pressure.

References to "prefillable" generally refer to syringes comprising components for filling with a substance prior to dispensing the substance for its intended use. More specifically, in the context of the syringe embodiments, the term "prefillable" refers to a configuration or state in which a substance may be introduced into the syringe any time prior to the dispensing by the syringe of the substance(s) for their intended use (such as delivery into a subject or device either directly or indirectly). A prefillable syringe thus includes syringes described herein as prefilled, fill-at-time-of-use, fill-on-demand, ready-to-use, and the like.

References to "pharmaceutical agent," "pharmaceutically active," "pharmaceutical," "drug," "medicament" "active agent," "active drug" and the like, refer in a general sense to substances useful in the medical and scientific arts as suitable for delivery via a syringe, including, for example, drugs, biologics, diagnostic agents (e.g, dyes or contrast agents) or other substances used for therapeutic, diagnostic, or preventative (e.g., vaccines), or research purposes. Example pharmaceutical agents include biologics, vaccines, chemotherapeutic agents, contrast agents, small molecules, immunogens, antigens, interferons, polyclonal antibody preparations, monoclonal antibodies, anesthetics, interfering RNAs, gene vectors, insulins, or combinations of any of these. "Inactive" substances refer to carriers, excipients, diluents, and the like, which are well-known in the art, although such substances may have beneficial function in the mixed injectable, such as, for example, adjuvants, isotonic or buffering agents. These active or inactive substances may also include substances having immediate, delayed or sustained release characteristics.

At least one embodiment provides for a connector comprising a distal portion configured to engage a luer fitment, a proximal syringe barrel-engaging portion comprising an axial ledge configured to abut an axial distal edge of a glass syringe barrel, and a fluid aperture axially therethrough.

At least one embodiment provides for syringe assembly comprising a glass barrel and a distal connector that includes a distal portion configured to engage a luer fitment, a proximal syringe barrel-engaging portion with an axial ledge configured to abut the axial distal edge of the glass barrel, and a fluid aperture therethrough. In some embodiments, the connector includes locking means that permanently connect the connector to a connection, such as a needle assembly. Some embodiments of the syringe assembly include a needle seal, located proximal to the connector and having a fluid aperture therethrough, in which the needle seal fluid aperture is configured to align with the connector fluid aperture to form a fluid passage. The needle seal can be constructed of an elastomeric material or a biocompatible material. The needle seal and connector may further include means for fixedly engaging with each other. Some embodiments of the syringe further include a tip cap having a body comprising a projection configured to engage the distal end of the connector fluid aperture and block fluid passage. The needle seal and the tip cap ensure that the drug fluid does not contact a non-compatible material during transportation and storage, i.e., prior to use. In particular embodiments, the projection extends through the connector at least into the needle seal. The projection can be constructed of an elastomeric material or a biocompatible material. The projection can be contiguous with or a separate piece of the tip cap. In some embodiments, the syringe includes a distal means for irreversibly indicating the tampering with, or use of, the connector. In some embodiments, the tip cap includes a means for irreversibly indicating the tampering with, or removal of, the tip cap.

At least one embodiment provides for a syringe comprising a glass barrel, a plunger, and a distal connector comprising a distal portion configured to engage a luer fitment; a proximal syringe barrel-engaging portion comprising an axial ledge configured to abut the axial distal edge of the glass barrel; and a fluid aperture therethrough. In some embodiments, this syringe further includes a needle seal, located proximal to the connector and having a fluid aperture therethrough, in which the needle seal fluid aperture is configured to align with the connector fluid aperture to form a fluid passage. Some embodiments of the syringe further include a tip cap having a body comprising a projection configured to engage the distal end of the connector fluid aperture and block fluid passage. The needle seal or the projection can be constructed of an elastomeric material or a biocompatible material. In some embodiments, the plunger includes a means for irreversibly indicating the tampering with, or use of, the plunger. In some embodiments, the tip cap includes a means for irreversibly indicating the tampering with, or removal of, the tip cap.

Another aspect of the present embodiments provides for prefilled syringes comprising connectors, in which the syringe is prefilled or prefillable with a substance. The substance can be a pharmaceutical agent. References to "pharmaceutical agent," refer in a general sense to substances useful in the medical and scientific arts as suitable for delivery via a syringe, including, for example, drugs, biologics, diagnostic agents (e.g, dyes or contrast agents) or other substances used for therapeutic, diagnostic, or preventative (e.g., vaccines), or research purposes. For example, the pharmaceutical agent can be a biologic, a vaccine, a chemotherapeutic agent, a contrast agent, a small molecule, an immunogen, an antigen, an interferon, a polyclonal antibody preparation, a monoclonal antibody, an anesthetic, an interfering RNA, a gene vector, an insulin, or a combination of any of these.

Figure 1B:
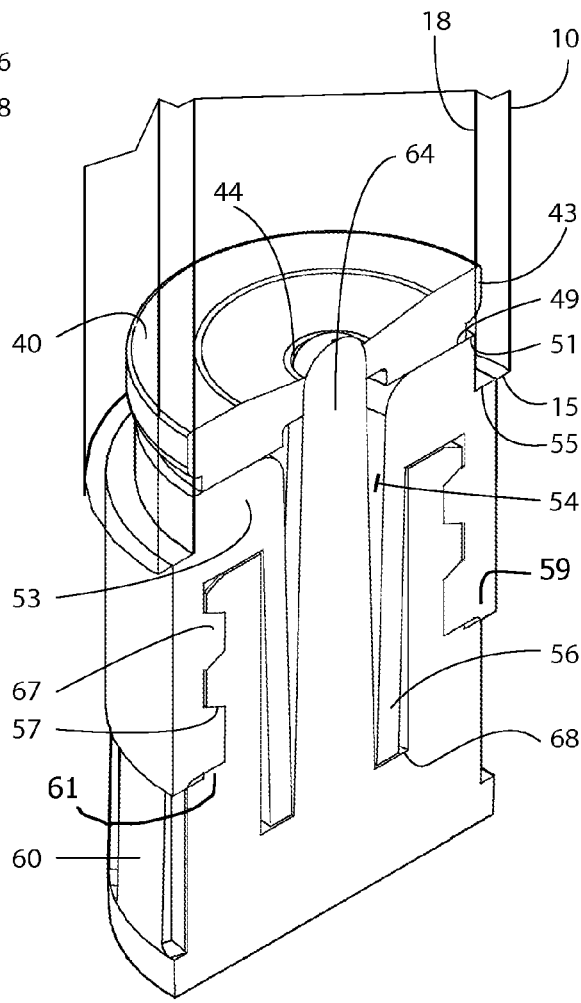
FIG. 1B is an isometric sectional view the embodiment of FIG. 1A.

Referring to FIG. 1, this figure shows an embodiment of a connector comprising a distal portion configured to engage a luer fitment and a proximal syringe barrel-engaging portion, which connector includes a fluid aperture axially therethrough. More specifically, luer connection adapter 50 disposed at the distal end of barrel 10 having a distal connection end 15 and interior wall 18. As shown in FIG. 1, barrel 10 is substantially cylindrical in shape, but the connectors described herein can be adapted for a variety of barrel shapes. The barrel can be formed of glass, but other resilient plastics or polymers may be used in manufacturing the barrel. As shown in FIG. 1, at distal connection end 15 of barrel 10 is mounted barrel connector 50. Connector 50 includes an axial ledge or shelf structure 55 configured to abut the distal barrel end 15, thus creating a connection point at which the abutting surfaces can be glued or otherwise permanently affixed to each other. For example, adhesive can be used to permanently connect the barrel and the adapter materials, such as glass and plastic, respectively. The adhesive is typically stable under sterilization and procedures, and storage and use conditions. The adhesive may be a curable adhesive, such as a heat-, time-, water- or UV-light-cured adhesive. The adhesive may be clear or colorless. Such adhesives are well known in the art. Alternatively, a connector can be pressure-connected into the barrel, for example by a design of portion of the adapter that sits within the barrel, such as 53, configured to press outwardly and immobily against the interior surface 18 of barrel 10. Barrel 10 further comprises inside wall 18 which, together with needle seal 40 and typical proximal syringe components such as a plunger, defines fluid space 12 inside barrel 10.

Figure 2A:
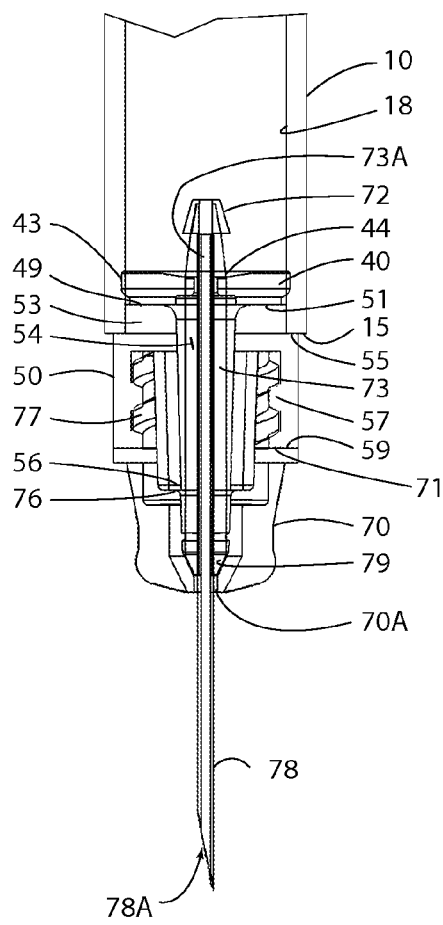
FIG. 2A is a sectional view of an embodiment of a connector having a needle assembly attached thereto.
Figure 2B:
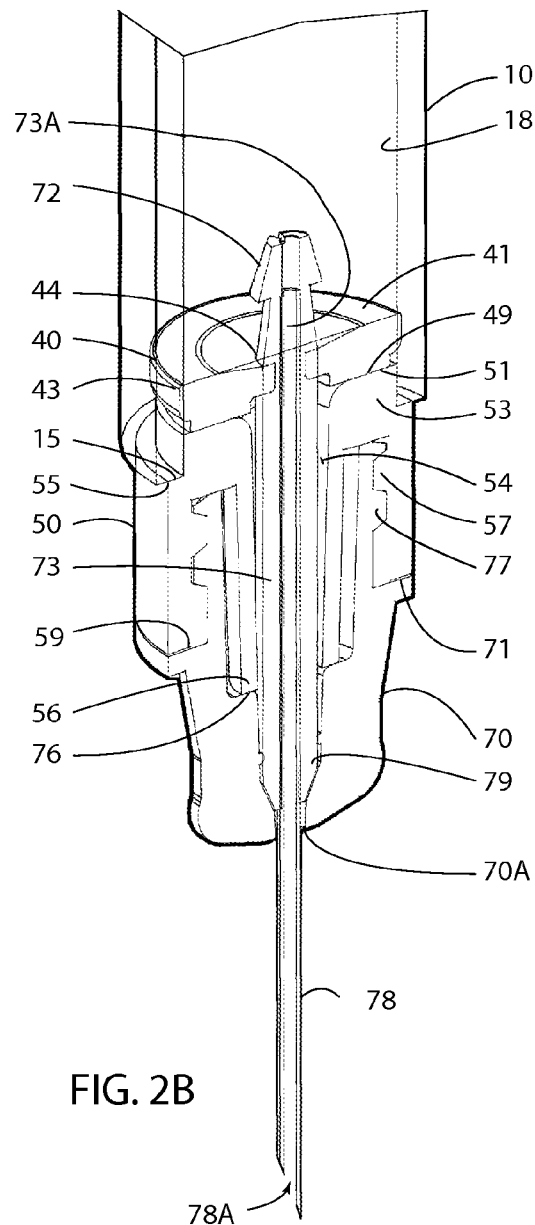
FIG. 2B is an isometric sectional view of the embodiment of FIG. 2A
Figure 3A:
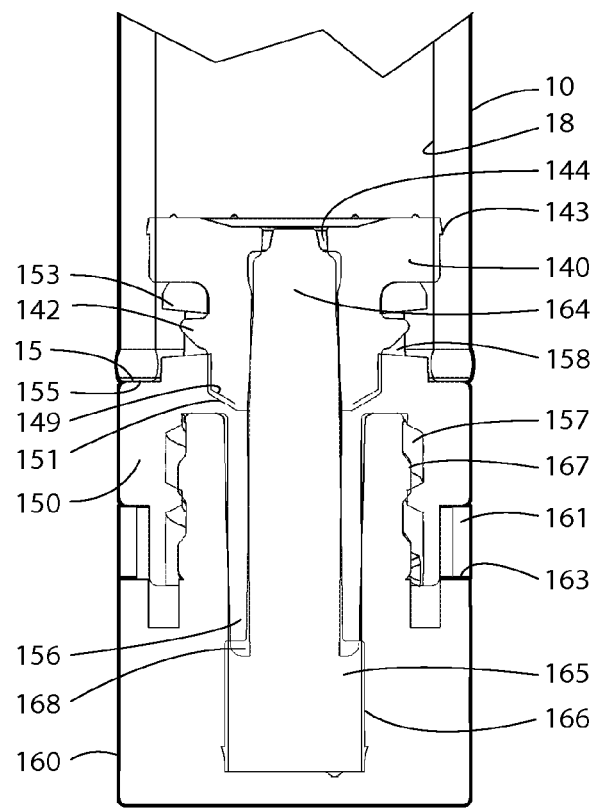
FIG. 3A is a sectional view of an alternative embodiment of a connector assembly and a removable tip cap.
Figure 3B:
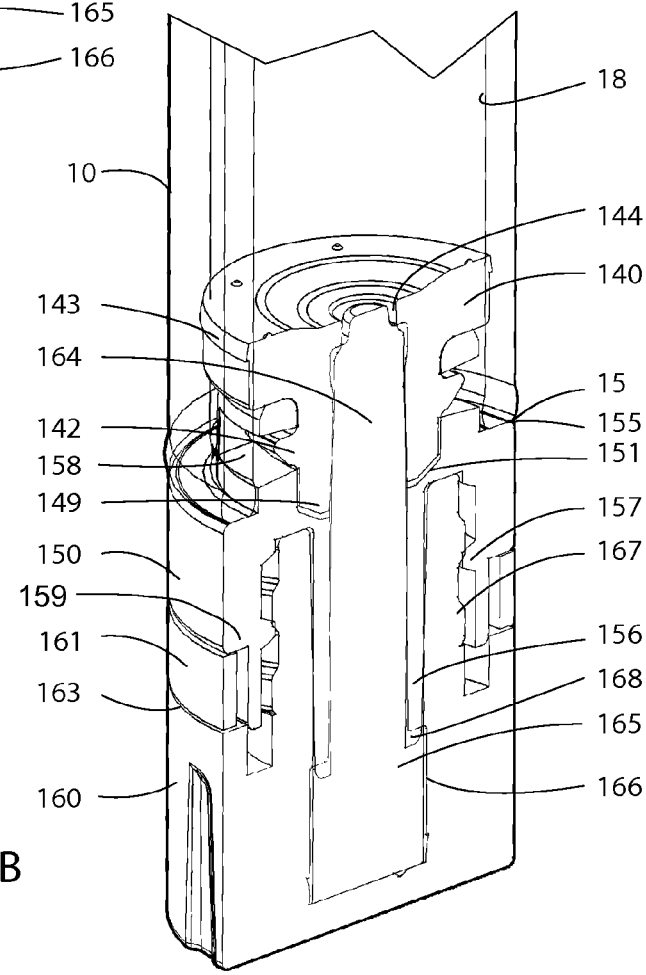
FIG. 3B is an isometric sectional view of the same embodiment.
Figure 3C:
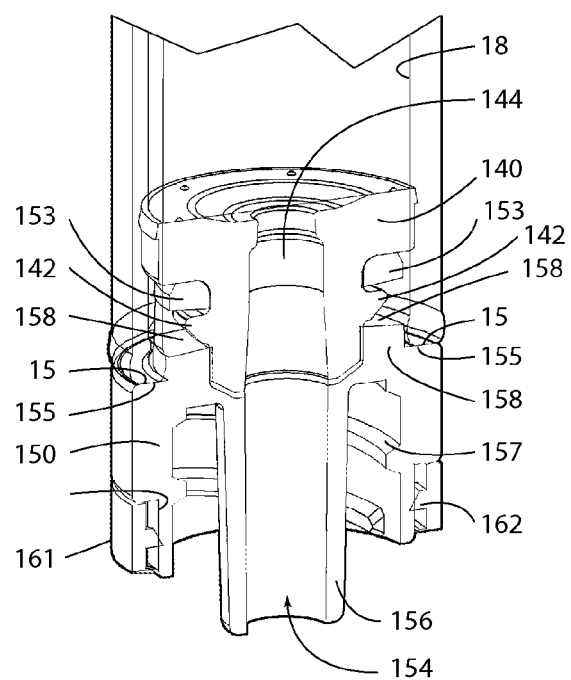
FIG. 3C is an isometric sectional view of the embodiment of FIG. 3A showing the tip cap removed.
Figure 3D:
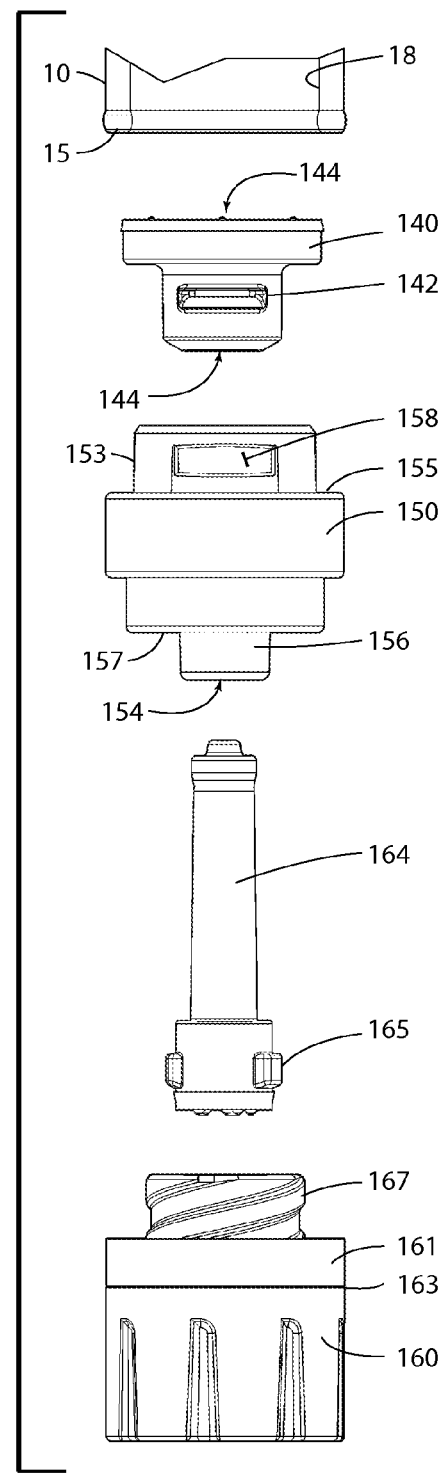
FIG. 3D is an exploded side view of the separate components of the embodiment of FIG. 3A.

With further reference to FIG. 1 and FIG. 2, connector 50 includes a luer connection portion comprising a distal luer lock connection having a tapered/conical aspect 56 and a screw-threaded mating structure 57. Connector 50 includes luer fitment 56 that extends distally from the end of syringe barrel 10. Luer fitment 56 is generally tubular and formed with a central, axial bore or fluid passageway extending axially there-through. The outside surface of the male luer fitment is tapered along the extending length to provide a surface sealingly mateable with the inner tapered surface of a female luer connector, thereby establishing a seat for and seal with a female luer hub. Luer adapter 50 further includes screw-thread 57 for further connecting to a luer connection, needle assembly, or other structure. For example, the female luer connector may be in the hub of a sharp needle assembly shown in FIG. 2, or as part of a fluid line, such as an intravenous fluid line, connection. Notably, adapter 50 has a center bore or central fluid passageway 54, which may be dimensioned to meet the necessary or desired requirements of the particular fluid or delivery mechanism.

Additionally, as shown in FIG. 1 and FIG. 2, the connector and barrel may further comprise an immobile, compressible elastomeric needle seal 40. The elastomeric needle seal is proximally adjacent to or engageable with the barrel-engaging portion of the adapter. More specifically, in the embodiments of FIG. 1 and FIG. 2, needle seal 40 sits within barrel 10 against interior wall 18, and proximal surface 51 of luer adapter 50 meets distal surface 49 of elastomeric needle seal 40. Needle seal 40 is configured with at least one radial, circumferential ring or rib 43 that bears against barrel interior wall 18 to form a liquid-tight seal. Needle seal 40 further comprises passage 44, configured to align with connector aperture 54. Needle seal 40 can be made of an elastomeric, rubber-based polymer that is particularly resilient to degradation or interaction with chemicals, pharmaceuticals or liquids in general, or may include such materials at proximal surface 41. In at least one embodiment, use of the elastomeric material of the needle seal is more desirable for contact with the contents of a syringe, particularly in prefillable syringes storage conditions, than are typical plastics used for syringes or molded syringe parts. Additionally, the connector can include tamper-resistant or tamper-evident components.

In the embodiment depicted in FIG. 1, connector 50 includes luer connection portion 57 and barrel-interior portion 53, a barrel-engaging portion 55 and aperture 54 there-through. The connector shelf or ledge 55 facilitates mounting the connector to distal barrel end 15. As shown in FIG. 1, the connector assembly may include tip cap 60 with proximal surface 61 that abuts distal surface 59 of connector 50; which tip cap includes a female luer fitment 68 for receiving male luer fitment 56, and screw thread 67 complementary to screw thread 57 of the distal luer fitment portion of connector 50. Tip cap 60 further includes elastomeric stem 64 that passes through channel 54 and needle seal channel 44. Stem 64 can be made integral to tip cap 60, or can be a separate component of the tip cap (see FIG. 3). In the configuration shown in FIG. 1, when the tip cap is in place, the contents of a prefilled syringe do not contact the plastic of the connector during storage. Instead, such contents contact only the elastomeric materials of needle seal 40 and the proximal end of stem 64, which can be formed from biocompatible materials. Tip cap 60 can be placed on luer connection adapter 50 before sterilization processes or under aseptic conditions such that it maintains sterility of the luer connector and syringe contents. This is particularly advantageous for use in prefilled syringes.

As shown in FIG. 2, a selectable needle assembly may be utilized and connected to the syringe to facilitate delivery to a user via injection. The needle assembly can be any appropriate needle or needle assembly, without limitation. In the embodiment of FIG. 2, luer connection adapter 50 may house a luer needle assembly having needle hub 70, wherein proximal end 71 of needle hub 70 abuts distal end 59 of the luer connection portion of connector 50. Needle hub 70 houses a first luer fitment 76 and screw thread 77 for connection to the corresponding luer fitment 56 and complementary screw thread 57 of adapter 50. Needle 78 is held in channel 73A of needle-over-mold 73, the distal end of the needle-over-mold 79 is held in channel 70A of needle hub 70. In the embodiment of FIG. 2, needle-over-mold 73 has proximal end 72, through which passes channel 73A. In this fashion, fluid communication is possible between and through the interior chamber 12 of barrel 10 and fluid channel 78A of needle 78. A variety of needle assemblies are compatible with the luer connection adapters described herein, such as, for example, needle assemblies described in U.S. Pat. No. 8,167,837.

Another embodiment of a connector as housed in a syringe includes a distal means for irreversibly indicating the tampering with, or use of, the connector. More specifically, for example, FIG. 3 shows connector 150 includes ledge 155, which abuts and is adhered to distal barrel connection point 15. A proximal portion 153 of connector 150 extends into barrel 10. Connector 150 also includes luer fitment 156 and a thread-screw configuration 157 for attachment to a tip cap, needle assembly, needle-less assembly (e.g., an i.v. luer line), and the like. In this embodiment, needle seal 140 is positioned within barrel 10, abutting its interior wall 18 and held in place by pressure exerted against surface 18 by ribs 143, or by interaction between protrusion 142 and window 158. Needle seal 140 further includes a locking means comprising protrusion or nub 142 configured to insert into or through an opening or window 158 in adapter 150, such that protrusion 142 and window 158 lock needle seal 140 and connector 150 in an engaged position. Needle seal 140 includes aperture 144, and distal end 149 that extends axially and distally within the proximal end of connector 150, received by complementary surface 151.

The embodiment of FIG. 3 further comprises tamper-evident tip cap 160. Tip cap 160 includes proximal portion 161 that abuts distal portion 159 of connector 150; which tip cap includes a female luer fitment 168 for receiving male luer fitment 156, and screw thread 167 complementary to screw thread 157 of the distal luer fitment portion of connector 150. Scored line 163 extends circumferentially around and partially, but not fully, through tip cap 160 distal to proximal portion 161, such that attempting to remove the cap provides biofeedback in the form of tangible resistance in attempting to remove the cap, a feeling of quick release when score line 163 is broken fully, and a slight noise like a snap or pop when score line 163 breaks and separates proximal portion 161 from the remainder of the cap structure. Therefore, if an operator finds that tip cap 160 is removed easily without resistance or noise, the operator may assume that the tip cap has been breached, and the device should not be used without consideration that the syringe contents may have been contaminated. Additionally, as shown in FIG. 3C, proximal portion 161 remains attached to connector 150, such as by tooth 162, even after the distal portion of cap 160 has been removed; providing visual feedback that the syringe may have been compromised if not used. In the embodiment of FIG. 3, tip cap 160 is made of resilient plastic to facilitate the tamper-evident features, and thus stem 164 is a separate elastomeric, drug-compatible stem that is seated in and held in place by tip cap cavity 166. Stem 164 may further comprise protrusions 165, shown particularly in FIG. 3D, to secure stem 164 within tip cap 160. Alternative mechanisms can be adapted for use with the connectors in relation to tamper-resistant devices, but in certain embodiments may lack the biofeedback (tactile) associated with breaking of tamper-resistant or tamper-evident seals.

FIG. 4A to FIG. 4C exemplify syringes that include some embodiments of connectors described herein. FIG. 4A shows a syringe assembly comprising a glass barrel; and a distal connector comprising a distal portion configured to engage a luer fitment and a proximal syringe barrel-engaging portion comprising an axial ledge configured to abut the axial distal edge of the glass barrel, and having a fluid aperture therethrough. More specifically, FIG. 4A shows a syringe that has barrel 10 with cap 13, in which interior wall 18 is suitable for contact with a substance housed in void 12. The embodiment of FIG. 4A further includes needle seal 40, having aperture 44 in fluid communication with aperture 54 of connector 50. Connector 50 further includes male luer fitment 56 and screw-threads 57 for connection to a needleless access device (such as an intravenous line), or a needle assembly, and the like. Connector 50 is connected at ledge 55 to the distal connection end 15 of barrel 10. Syringes comprising plungers can include, for example, standard plungers known in the art.

As shown in FIG. 4B and FIG. 4C, The syringe can further include a needle seal, located proximal to the connector, having a fluid aperture therethrough, wherein the needle seal fluid aperture is configured to align with the connector fluid aperture to form a fluid passage. As shown in FIG. 4B, the syringe may be capped at the distal end by a tip cap. As described herein, an elastomeric tip cap, for example, may be used for this purpose though plastic tip caps and tip caps of other materials may also be utilized. If the syringe is to be utilized with a needle assembly, a needle assembly may be contained in a needle cap. FIG. 4C shows a syringe with the needle assembly connected via the connector 50. A needle cap, such as needle cap 75, containing the needle assembly may be utilized to safely connect the needle assembly to the syringe (i.e., without exposure to the needle).

The embodiments of the present invention may further utilize additional components to enhance the use of the syringe, such as tamper-resistance aspects to prevent tampering of the syringe. These tamper-resistance aspects deter or prevent an unauthorized user from, for example, removing the plunger rod, or provide evidence of tampering such that an unauthorized user will be discouraged from compromising the syringe. These tamper-resistance aspects could be located along the plunger rod, plunger seal, or the barrel flange, collar, or release ring. These tamper-resistance aspects could be axially positioned or longitudinally oriented, or in a number of other known configurations.

Each of the embodiments described herein may be used alone or in combination with one or more other embodiments in a syringe. Throughout the specification, the aim has been to describe the preferred embodiments of the invention without limiting the invention to any one embodiment or specific collection of features. Various changes and modifications may be made to the embodiments described and illustrated without departing from the present invention. The disclosure of each patent and scientific document, computer program and algorithm referred to in this specification is incorporated by reference in its entirety.

What is claimed is:

1. A syringe assembly comprising
a barrel that is substantially straight from a first proximal end to a second distal end of the barrel;
a distal connector comprising an axial ledge separating the distal connector into a distal portion comprising a luer fitment and a thread-screw configuration, and a proximal portion, configured to engage an interior wall within the distal end of the barrel, and a distal connector fluid aperture therethrough, wherein the axial ledge is configured to abut the distal end of the barrel; and
a needle seal, located at least partially proximal to the distal connector, having a needle seal fluid aperture therethrough, wherein the needle seal fluid aperture is configured to align with the distal connector fluid aperture to form a fluid passage.

2. The syringe assembly of claim 1, wherein the needle seal is constructed of an elastomeric material or a biocompatible material.

3. The syringe assembly of claim 1, further comprising a tip cap having a body comprising a projection configured to engage the distal end of the distal connector fluid aperture and block fluid passage.

4. The syringe assembly of claim 3, wherein the projection is constructed of an elastomeric material or a biocompatible material.

5. The syringe assembly of claim 1, further comprising a distal means for irreversibly indicating the tampering with, or use of, the connector.

6. A syringe comprising
a barrel that is substantially straight from a first proximal end to a second distal end of the barrel;
a plunger;
a distal connector comprising an axial ledge separating the distal connector into a distal portion comprising a luer fitment and a thread-screw configuration, and a proximal portion, configured to engage an interior wall within the distal end of the barrel, and a distal connector fluid aperture therethrough, wherein the axial ledge is configured to abut the distal end of the barrel; and
a needle seal, located at least partially proximal to the distal connector, having a needle seal fluid aperture therethrough, wherein the needle seal fluid aperture is configured to align with the distal connector fluid aperture to form a fluid passage.

7. The syringe assembly of claim 6, wherein the needle seal is constructed of an elastomeric material or a biocompatible material.

8. The syringe of claim 6, further comprising a tip cap having a body comprising a projection configured to engage the distal end of the distal connector fluid aperture and block fluid passage.

9. The syringe assembly of claim 8 wherein the projection is constructed of an elastomeric material or a biocompatible material.

10. The syringe of claim 6 wherein the plunger comprises a means for irreversibly indicating the tampering with, or use of, the plunger.

11. The syringe of claim 6 wherein the syringe is prefilled with a substance.

12. The syringe of claim 11 wherein the substance comprises a pharmaceutical agent.

13. The syringe of claim 12 wherein the pharmaceutical agent is selected from the group consisting of a biologic, a vaccine, a chemotherapeutic agent, a contrast agent, a small molecule, an immunogen, an antigen, an interferon, a polyclonal antibody preparation, a monoclonal antibody, an anesthetic, an interfering RNA, a gene vector, an insulin, and a combination of any of these.

* * * * *